(12) United States Patent
Knöpfle et al.

(10) Patent No.: US 9,155,576 B2
(45) Date of Patent: Oct. 13, 2015

(54) BONE ANCHOR, ORTHOPAEDIC DEVICE AND ORTHOPAEDIC SYSTEM (75) Inventors: Christian Knöpfle, Donaueschingen (DE); Regine Maurer, Freiburg (DE)

(73) Assignee: Stryker Leibinger GmbH & Co. KG (DE)

( * ) Notice: Subject to any disclaimer, the term of this patent is extended or adjusted under 35 U.S.C. 154(b) by 412 days.

(21) Appl. No.: 12/869,034

(22) Filed: Aug. 26, 2010

(65) Prior Publication Data
US 2011/0054539 A1 Mar. 3, 2011

(30) Foreign Application Priority Data
Aug. 27, 2009 (EP) ..................................... 09011011

(51) Int. Cl.
*A61B 17/80* (2006.01)
*A61B 17/66* (2006.01)
*A61B 17/68* (2006.01)

(52) U.S. Cl.
CPC ............. *A61B 17/8004* (2013.01); *A61B 17/80* (2013.01); *A61B 17/8019* (2013.01); *A61B 17/66* (2013.01); *A61B 2017/681* (2013.01)

(58) Field of Classification Search
CPC .... A61B 17/663; A61B 17/666; A61B 17/80; A61B 17/8004; A61B 17/8019; A61B 17/8071
USPC ......... 606/57, 58, 252, 257, 90, 105, 280, 70, 606/71, 282–285; 623/17.17–17.19; 433/7
See application file for complete search history.

(56) References Cited

U.S. PATENT DOCUMENTS

| 1,105,105 | A | * | 7/1914 | Sherman | 606/286 |
|---|---|---|---|---|---|
| 5,129,903 | A | | 7/1992 | Luhr et al. | |
| 5,139,498 | A | * | 8/1992 | Astudillo Ley | 606/281 |
| 5,372,598 | A | | 12/1994 | Luhr et al. | |
| 5,855,580 | A | | 1/1999 | Kreidler et al. | |
| 5,980,540 | A | * | 11/1999 | Bruce | 606/151 |
| 6,471,706 | B1 | | 10/2002 | Schumacher et al. | |
| 6,652,530 | B2 | * | 11/2003 | Ip et al. | 606/284 |
| 6,786,910 | B2 | | 9/2004 | Cohen et al. | |
| 7,335,207 | B1 | * | 2/2008 | Smith | 606/99 |
| 7,621,922 | B2 | | 11/2009 | Schendel et al. | |
| 2002/0128654 | A1 | * | 9/2002 | Steger et al. | 606/69 |
| 2002/0133157 | A1 | | 9/2002 | Sterett et al. | |
| 2004/0102777 | A1 | | 5/2004 | Huebner | |
| 2005/0209594 | A1 | * | 9/2005 | Sellers | 606/71 |
| 2005/0256526 | A1 | | 11/2005 | Johnston | |
| 2006/0015118 | A1 | | 1/2006 | Richter et al. | |
| 2006/0079902 | A1 | * | 4/2006 | Johnston | 606/71 |
| 2006/0276794 | A1 | * | 12/2006 | Stern | 606/69 |

* cited by examiner

*Primary Examiner* — Michael T Schaper
(74) *Attorney, Agent, or Firm* — Lerner, David, Littenberg, Krumholz & Mentlik, LLP (57) ABSTRACT

A bone anchor, orthopaedic device and orthopaedic system are described. A bone anchor for use in an orthopaedic procedure which comprises a bone fixation portion provided with a plurality of fixation openings, the fixation openings each being adapted to receive a fixation device for fixing the bone fixation portion to a bone of a patient, and a device attachment portion provided with a first attachment opening and a second attachment opening, the first attachment opening and the second attachment opening being connected to each other by a solid stabilizing portion and being adapted to receive an attachment device for attaching the device attachment portion to an orthopaedic device.

19 Claims, 6 Drawing Sheets

BONE ANCHOR, ORTHOPAEDIC DEVICE AND ORTHOPAEDIC SYSTEM

CROSS-REFERENCE TO RELATED APPLICATIONS

This application claims the benefit of the filing date of European Application No. 09 011 011.5 filed Aug. 27, 2009, the disclosure of which is hereby incorporated herein by reference.

BACKGROUND OF THE INVENTION

The invention relates to a bone anchor, an orthopaedic device and an orthopaedic system for use in an orthopaedic procedure, in particular an osteotomy procedure.

An osteotomy is a surgical operation whereby a bone is cut, for example, to shorten or lengthen the bone, to change its alignment or to remove a diseased part of the bone. After cutting the bone, typically bone anchors are attached to bone regions on both sides of the cut which serve to connect an orthopaedic device to the bone regions. Orthopaedic devices which can be used in an osteotomy procedure include fixation devices for stabilizing the cut bone regions, reduction devices for gradually shortening a distance between the cut bone regions, distraction devices for gradually lengthening a distance between the cut bone regions, and devices for adjusting the relative orientation of the cut bone regions.

A distraction device, which, by means of two bone plates, is attachable to a bone to be treated, is known for example from DE 298 13 087 U1. The bone plates each comprise a plurality of openings adapted to receive suitable bone screws for fastening the bone plates to bone. In addition, a further opening provided in each of the bone plates serves to receive a fastening screw for fastening the bone plate to a fixed retainer and a moveable retainer of a distractor housing, respectively.

BRIEF SUMMARY OF THE INVENTION

The invention is directed to the object to provide a bone anchor, an orthopaedic device and an orthopaedic system for use in an orthopaedic procedure, in particular an osteotomy procedure, which allow to particularly securely attach an orthopaedic device to a patient's bone to be treated.

A first aspect of the present invention is a bone anchor for use in an orthopaedic procedure. The bone anchor comprises a bone fixation portion, which is adapted to contact a bone of a patient to be treated. The bone fixation portion is provided with a plurality of fixation openings, the fixation openings each being adapted to receive a fixation device, such as e.g. a bone screw, for fixing the bone fixation portion to the patient's bone. Preferably, a shape of the fixation openings is adapted to the shape of the fixation devices to be received in the fixation openings. In particular, a cross-section of the fixation openings may be adapted to a cross-section of the fixation devices to be received in the fixation openings.

Further, the bone fixation portion, in a surface that faces away from the patient's bone when the bone anchor is attached to the patient's bone, might be provided with recesses or lowerings surrounding the fixation openings. The shape of the recesses or lowerings may be adapted to the shape of a head of the fixation devices to be received in the fixation openings. Preferably, the recesses or lowerings are shaped such that the fixation devices do not protrude from the surface of the bone fixation portion, which faces away from the patient's bone when the bone anchor is attached to the patient's bone. Thereby, a flat overall shape of the bone fixation portion is achieved. As a result, the bone anchor is less obstructing to a patient when attached to the patient's bone.

The bone anchor according to one embodiment of the first aspect of the invention further comprises a device attachment portion, which is adapted to contact a corresponding bone anchor attachment portion of an orthopaedic device. The orthopaedic device may be a fixation device, a reduction device, a distraction device or a device for adjusting the relative orientation of a patient's bone regions. The orthopaedic device preferably is a device for use in an osteotomy procedure.

The device attachment portion of the bone anchor according to one embodiment of the first aspect of the present invention is provided with a first attachment opening and a second attachment opening, the first attachment opening and the second attachment opening each being adapted to receive an attachment device, such as a screw, a clip or another suitable attachment device for attaching the device attachment portion to the orthopaedic device, preferably the bone anchor attachment portion of the orthopaedic device.

Preferably, a shape of the first attachment opening and the second attachment opening is adapted to the shape of the attachment devices to be received in the first attachment opening and the second attachment opening. In particular, a cross-section of the first attachment opening and the second attachment opening may be adapted to a cross-section of the attachment devices to be received in the first attachment opening and the second attachment opening.

The device attachment portion might also be provided with fixation openings. Preferably, however, all fixation openings are formed in the bone fixation portion of the bone anchor such that the device attachment portion is provided only with at least the first attachment opening and the second attachment opening. If desired or necessary to securely attach the bone anchor to an orthopaedic device, the device attachment portion may comprise more than two attachment openings being adapted to receive a suitable attachment device for attaching the device attachment portion to the orthopaedic device.

The first attachment opening and the second attachment opening are preferably connected to each other by a solid stabilizing portion. The solid stabilizing portion is preferably not provided with any attachment or fixation openings, but is formed from a solid material. Preferably, the design of the bone anchor obtains a device attachment portion wherein the mechanical strength of which is not affected by an excessive number of attachment openings and/or fixation openings. Instead, the solid stabilizing portion provides for a high stiffness and torsion resistance of the device attachment portion. As a result, the bone anchor according to the invention allows to particularly securely attach an orthopaedic device to a patient's bone to be treated.

A distance between the first attachment opening and the second attachment opening, for example, an extension of the solid stabilizing portion between the first attachment opening and the second attachment opening, preferably is greater than a distance between the first attachment opening and an adjacent fixation opening, a distance between the second attachment opening and an adjacent fixation opening and/or a distance between adjacent fixation openings. The distance between the first attachment opening and the second attachment opening might only be greater than the distance between the first attachment opening and an adjacent fixation opening, the distance between the second attachment opening and an adjacent fixation opening or the distance between selected adjacent fixation openings. Preferably, however, the distance between the first attachment opening and the second attachment opening is greater than the distances between all fixation openings disposed adjacent to each other. In one embodiment of the bone anchor, the distance between the first attachment opening and the second attachment opening, for example, the extension of the solid stabilizing portion between the first attachment opening and the second attachment opening is greater than any distances between any kind of openings provided in the bone anchor.

Preferably, the first attachment opening, the second attachment opening and the plurality of fixation openings are disposed in a row pattern, wherein the rows of openings in the row pattern may extend substantially parallel to each other. Further, the attachment openings and the fixation openings may define a rectangular row pattern including one or more row(s) of openings extending in a first direction and one or more row(s) of openings extending in a second direction perpendicular to the first direction. It is, however, also possible that the rows of openings in the row pattern extend in arbitrary directions such that an irregular row pattern is defined. Attachment openings and fixation openings disposed in a row pattern allow the bone anchor according to the invention to be securely fixed to the bone of a patient and an orthopaedic device, wherein the design of the row pattern easily can be adjusted to specific application requirements, for example, the shape of the patient's bone to be treated and the shape of the bone anchor attachment portion of the orthopaedic device.

The first attachment opening and the second attachment opening might be disposed in a first row of the row pattern. The first row might include only the first attachment opening and the second attachment opening. Alternatively, the first row, beside the first attachment opening and the second attachment opening, might also include further attachment openings and/or one or more fixation opening(s).

A plurality of fixation openings might be disposed in at least a second row of the row pattern disposed adjacent to the first row of the row pattern. The row pattern might have only two rows of openings, namely a first row including at least the first attachment opening and the second attachment opening, and a second row defined by a plurality of fixation openings. It is, however, also possible to provide the row pattern with a plurality of rows disposed adjacent to each other. In such an embodiment, a first row preferably is formed by at least the first attachment opening and the second attachment opening, wherein any further rows, i.e. the second row, a third row, a fourth row etc., are defined by a plurality of fixation openings. In such a configuration, at least the part of the first row including the first attachment opening and the second attachment opening can be associated with the device attachment portion of the bone anchor, whereas any further rows of the row pattern which are defined by fixation openings can be associated with the bone fixation portion of the bone anchor.

A distance between the first row of the row pattern, which preferably includes at least the first attachment opening and the second attachment opening, and the second row of the row pattern, which preferably is defined by a plurality of fixation openings, may be greater than a distance between the second row of the row pattern and an adjacent third row of the row pattern. Preferably, the distance between the first row of the row pattern and the second row of the row pattern is greater than the distances between any further rows of the row pattern, for example, the distance between the second row of the row pattern and an adjacent third row of the row pattern, the third row of the row pattern and an adjacent fourth row of the row pattern, the fourth row of the row pattern and an adjacent fifth row of the row pattern, etc. Such a design of the row pattern ensures that an orthopaedic device can securely be attached to the device attachment portion of the bone anchor according to the invention by means of suitable attachment devices received in the first attachment opening and the second attachment opening disposed in the first row of the row pattern. Simultaneously, fixation of the bone fixation portion of the bone anchor according to the invention by means of suitable fixation devices received in the fixation openings disposed in the second, third, fourth, etc. rows of the row pattern is not impeded by the orthopaedic device.

The distances between the rows of the row pattern following the second row, for example, the distance between the second row and the third row, the distance between the third row and the fourth row, the distance between the fourth row and the fifth row, etc. might be equal to each other. It is, however, also possible to vary the distances between adjacent rows of the row pattern to adapt the bone anchor according to the invention to specific anatomic requirements of a patient's bone to be treated.

The first row of the row pattern, which preferably includes at least the first attachment opening and the second attachment opening, may be disposed at any position within the row pattern, for example, the first row of openings, at least over a part of its length, on two sides might be flanked by adjacent rows of openings. Preferably, however, the first row of the row pattern, which might include at least the first attachment opening and the second attachment opening, forms an edge row of the row pattern with the first row of openings on only one side being flanked by an adjacent row of openings. When the bone anchor according to the invention is connected to an orthopaedic device, the first row of the row pattern, which includes at least the first attachment opening and the second attachment opening, preferably faces the orthopaedic device.

In a preferred embodiment of the bone anchor according to the invention, the solid stabilizing portion connecting the first attachment opening and the second attachment opening has a bar-shaped configuration. Adjacent fixation openings may be connected by a bar-shaped bridging portion. A bone anchor which is provided with a bar-shaped solid stabilizing portion and/or bar-shaped bridging portions can be particularly lightweight. In addition, the bone anchor still has some flexibility which simplifies fixation of the bone anchor to the complex shape of a patient's bone.

Preferably, the solid stabilizing portion connecting the first attachment opening and the second attachment opening is broader than the bridging portion(s) connecting adjacent fixation openings. In this context, the term "broader" means that the solid stabilizing portion in a direction perpendicular to an axis connecting the first attachment opening and the second attachment opening has a greater extension than the bridging portion(s) in a direction perpendicular to an axis connecting the adjacent fixation openings. The solid stabilizing portion may only be broader than (a) selected bridging portion(s) connecting selected adjacent fixation openings. Preferably, however, the solid stabilizing portion is broader than all bridging portions connecting adjacent fixation openings.

The bone anchor according to the invention preferably further comprises at least one connecting portion extending between the first attachment opening and an adjacent fixation opening, between the solid stabilizing portion and an adjacent fixation opening, and/or between the second attachment opening and an adjacent fixation opening. (A) connecting portion(s) might be provided between the first attachment opening and a fixation opening disposed in a row of openings extending in the direction of the axis connecting the first attachment opening and the second attachment opening, for example, the first row of openings, and/or between the first attachment opening and a fixation opening disposed in a row of openings extending at least partially substantially parallel to the axis connecting the first attachment opening and the second attachment opening, for example, the second row of openings. Similarly, (a) connecting portion(s) might be provided between the second attachment opening and a fixation opening disposed in a row of openings extending in the direction of the axis connecting the first attachment opening and the second attachment opening, for example, the first row of openings, and/or between the second attachment opening and a fixation opening disposed in a row of openings extending at least partially substantially parallel to the axis connecting the first attachment opening and the second attachment opening, for example, the second row of openings. A connection portion associated with the solid stabilizing portion typically connects the solid stabilizing portion to a fixation opening disposed in a row of openings which extends at least partially substantially parallel to the axis connecting the first attachment opening and the second attachment opening, for example, the second row of openings.

At least a part of the connecting portion(s) preferably is adapted to contact a bone anchor attachment portion of an orthopaedic device, when the bone anchor according to the invention is attached to the orthopaedic device. In other words, at least a part of the connecting portion(s) preferably is adapted to abut against a surface of the bone anchor attachment portion of the orthopaedic device, when the bone anchor is attached to the orthopaedic device. As a result, the connection portion(s) and in particular the connecting portion extending between the solid stabilizing portion and an adjacent fixation opening, enhance(s) the stability and torsion resistance of the connection between the bone anchor and the orthopaedic device.

The extension of the connecting portion(s) in a direction of an axis connecting the first attachment opening to an adjacent fixation opening disposed in an adjacent row of openings, an axis connecting the solid stabilizing portion to an adjacent fixation opening, or an axis connecting the second attachment opening to an adjacent fixation opening disposed in an adjacent row of openings typically depends on the distance between the first row of openings containing at least the first attachment opening and the second attachment opening and an adjacent second row of openings containing the fixation opening(s) disposed adjacent to the first attachment opening, the solid stabilizing portion and/or the second attachment opening. If the distance between the first row of openings and the second row of openings is greater than the distances between further rows of openings, the extension of the connecting portion(s) is greater than the extension of the majority of the bridging portions in a direction of an axis connecting the adjacent fixation openings. Only bridging portion extending between fixation openings which, beside the first attachment opening and the second attachment opening, are disposed in the first row of openings and fixation openings disposed in an adjacent second row of openings then might have an extension which is equal to the extension of the connecting portion(s).

At least one of the first attachment opening and the second attachment opening, i.e. an inner surface of at least one of the first attachment opening and the second attachment opening, may be provided with an internal thread. The internal thread preferably is adapted to interact with a corresponding external thread provided on an outer surface of the attachment device which is used to attach the device attachment portion of the bone anchor according to the invention to a bone anchor attachment portion of an orthopaedic device. Such a configuration allows an orthopaedic device to easily be attached to and detached from the bone anchor according to the invention, e.g. by means of suitable screws.

An orthopaedic device according to the invention for use in an orthopaedic procedure comprises a treatment portion adapted to perform a desired orthopaedic treatment to a bone of a patient. The treatment portion might be adapted to perform an osteotomy procedure, such as e.g. a fixation procedure, a reduction procedure, a distraction procedure or a procedure for adjusting the relative orientation of a patient's bone regions. Preferably, the treatment portion includes a distraction device.

The orthopaedic device further comprises a bone anchor attachment portion provided with a first attachment opening and a second attachment opening. The first attachment opening and the second attachment opening are adapted to receive an attachment device for attaching the bone anchor attachment portion to an above described bone anchor. At least one of the first attachment opening and the second attachment opening, i.e. an inner surface of at least one of the first attachment opening and the second attachment opening, might be provided with an internal thread. Preferably, the attachment openings provided in the bone anchor attachment portion of the orthopaedic device and the attachment openings provided in the device attachment portion of the bone anchor are positioned such that the first attachment opening of the bone anchor attachment portion of the orthopaedic device coincides with the first attachment opening of the device attachment portion of the bone anchor, and such that the second attachment opening of the bone anchor attachment portion of the orthopaedic device coincides with the second attachment opening of the device attachment portion of the bone anchor, when the bone anchor attachment portion of the orthopaedic device and the device attachment portion of the bone anchor are attached to each other.

A contact surface of the bone anchor attachment portion of the orthopaedic device according to the invention with the bone anchor, i.e. a contact surface of the bone anchor attachment portion of the orthopaedic device with the device attachment portion of the bone anchor, is provided with a recess, the shape of which is adapted to the shape of the device attachment portion of the bone anchor. The recess might have a portion adapted to receive the solid stabilizing portion connecting the first attachment opening and the second attachment opening provided in the device attachment portion of the bone anchor. Further, the recess might have portions adapted to receive at least a part of at least one connecting portion extending between the first attachment opening and an adjacent fixation opening, between the solid stabilizing portion and an adjacent fixation opening, or between the second attachment opening and an adjacent fixation opening of the bone anchor.

By providing the contact surface of the bone anchor attachment portion of the orthopaedic device according to the invention with the bone anchor with a recess, the shape of which is adapted to the shape of the device attachment portion of the bone anchor, a particularly secure, stiff and torsion resistant connection between the orthopaedic device and the bone anchor can be achieved. In addition, the overall height of the bone anchor and the orthopaedic device in the connected state can be reduced. As a result, the bone anchor and the orthopaedic device are less obstructing to a patient when attached to the patient's bone.

Preferably, the depth of the recess provided in the contact surface of the bone anchor attachment portion with the bone anchor is selected such that the device attachment portion of the bone anchor is entirely received in the recess. In other words, the depth of the recess provided in the contact surface of the bone anchor attachment portion with the bone anchor preferably is selected such that a surface of the device attachment portion of the bone anchor is disposed flush with portions of the contact surface surrounding the recess. As a result, a particularly flat configuration of the bone anchor and the orthopaedic device in the connected state is achieved.

An orthopaedic system according to the invention comprises at least one above described bone anchor and an above described orthopaedic device. The bone anchor may have any desired shape. For example the bone anchor may be in the form of a flat plate. The bone anchor, however, may also have a curved shape or a three-dimensional shape. Further, the bone anchor also may be customized, i.e. specifically adapted to a patient's bone. Finally, the bone anchor may be made of any desired material including biocompatible materials, such as e.g. titanium or titanium alloys, or bioresorbable or bioabsorbable materials.

Preferably, the orthopaedic system according to the invention comprises a plurality of differently shaped sets of above described bone anchors. The orthopaedic system then can be used to treat differently shaped bones.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
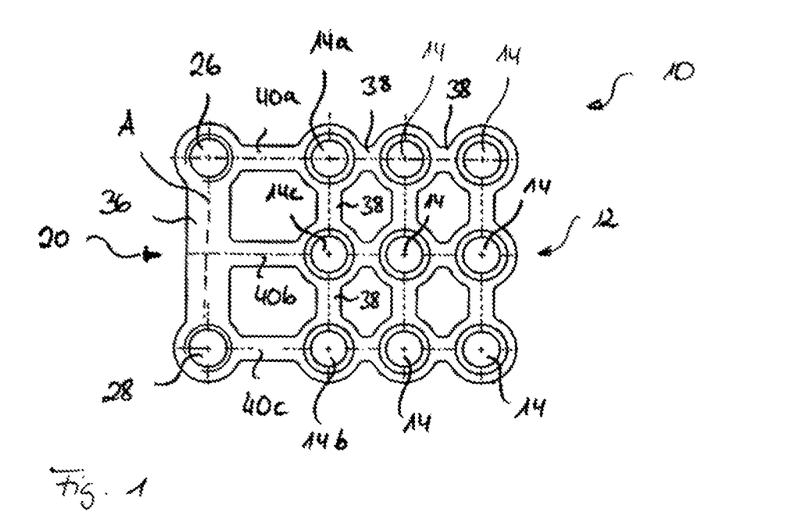
FIG. 1 shows an embodiment of a bone anchor for use in an orthopaedic procedure.
Figure 2:
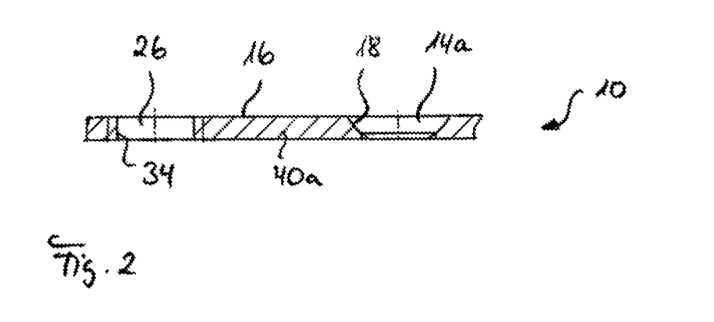
FIG. 2 shows a cross sectional view of a portion of the bone anchor shown in FIG. 1.

FIGS. 1 and 2 show a bone anchor 10 for use in an orthopaedic procedure, in particular an osteotomy distraction procedure. The bone anchor 10 comprises a bone fixation portion 12 which is adapted to contact a bone of a patient to be treated.

The bone fixation portion 12 is provided with a plurality of fixation openings 14, the fixation openings each being adapted to receive a bone screw (not shown), for fixing the bone fixation portion 12 to the patient's bone. A cross-section of the fixation openings 14 is adapted to a cross-section of the bone screws to be received in the fixation openings 14. Further, as becomes apparent from FIG. 2, the bone fixation portion 12 includes a surface 16, which faces away from the patient's bone when the bone anchor 10 is attached to the patient's bone. Bone fixation portion preferably includes recesses 18 surrounding the fixation openings 14. The shape of the recesses 18 is adapted to the shape of a head of the bone screws to be received in the fixation openings 14. Thereby, a flat overall shape of bone fixation portion 12 is obtained. The bone anchor 10 and the bone screws are made of titanium or a titanium alloy. It is, however, also possible to manufacture the bone anchor 10 and the bone screws from a bioresorbable material.

The bone anchor 10 further comprises a device attachment portion 20 which is adapted to contact corresponding bone anchor attachment portions 22a, 22b of an orthopaedic distraction device 24 which is illustrated in FIGS. 10 to 14. The device attachment portion 20 of the bone anchor 10 is provided with a first attachment opening 26 and a second attachment opening 28. Similarly, each bone anchor attachment portion 22a, 22b of the orthopaedic distraction device 24 is provided with a first attachment opening 30 and a second attachment opening 32. The attachment openings 30, 32 provided in the bone anchor attachment portions 22a, 22b of the orthopaedic distraction device 24 and the attachment openings 26, 28 provided in the device attachment portion 20 of the bone anchor 10 are positioned such that the first attachment opening 30 of a bone anchor attachment portion 22a, 22b of the orthopaedic distraction device 24 coincides with the first attachment 26 opening of the device attachment portion 20 of the bone anchor 10, and such that the second attachment opening 32 of the bone anchor attachment portion 22a, 22b of the orthopaedic distraction device 24 coincides with the second attachment opening 28 of the device attachment portion 20 of the bone anchor 10, when the bone anchor attachment portion 22a, 22b of the orthopaedic distraction device 24 and the device attachment portion 20 of the bone anchor 10 are attached to each other.

The attachment openings 26, 28, 30, 32 are adapted to receive an attachment device 33, such as e.g. a screw, for attaching the device attachment portion 20 of the bone anchor to a bone anchor attachment portion 22a, 22b of the orthopaedic distraction device 24. To facilitate the fastening of screws in the attachment openings 26, 28 provided in the device attachment portion 20 of the bone anchor 10, an inner surface of the first attachment opening 26 and the second attachment opening 28 is provided with an internal thread 34 (see FIG. 2) which is adapted to interact with a corresponding external thread provided on an outer surface of the attachment device 33 to be received in the attachment openings 26, 28, 30, 32. Similarly, an inner surface of the attachment openings 30, 32 provided in the bone anchor attachment portion 22a, 22b of the orthopaedic distraction device 24 is provided with an internal thread 37 (see FIG. 14) which is adapted to interact with a corresponding external thread provided on an outer surface of the attachment device 33 to be received in the attachment openings 26, 28, 30, 32.

A surface 35 of the bone anchor attachment portions 22a, 22b of the orthopaedic distraction device 24 which faces away from the bone anchor 10, when a bone anchor 10 is attached to the bone anchor attachment portions 22a, 22b of the orthopaedic distraction device 24, in a region surrounding the attachment openings 30, 32 is provided with a lowering or indentation so as to guide a tool for interacting with the screw to be received in the attachment openings 26, 28, 30, 32.

The first attachment opening 26 and the second attachment opening 28 of the device attachment portion 20 are connected to each other by a solid stabilizing portion 36. The solid stabilizing portion 36 is not provided with any attachment or fixation openings, but is formed from a solid material. A distance between the first attachment opening 26 and the second attachment opening 28, i.e. an extension of the solid stabilizing portion 36 between the first attachment opening 26 and the second attachment opening 28, is greater than a distance between the first attachment opening 26 and an adjacent fixation opening 14a, a distance between the second attachment opening 28 and an adjacent fixation opening 14b and a distance between any adjacent fixation openings 14.

The first attachment opening 26, the second attachment opening 28 and the plurality of fixation openings 14 are disposed in a row pattern, wherein the rows of openings in the row pattern extend substantially parallel to each other. Further, the attachment openings 26, 28 and the fixation openings 14 define a rectangular row pattern including four rows of openings extending in a first direction corresponding to a direction of an axis A connecting the first attachment opening 26 and the second attachment opening 28, and three rows of openings extending in a second direction perpendicular to the first direction. The first attachment opening 26 and the second attachment opening 28 are disposed in a first edge row of the row pattern which includes only the first attachment opening 26 and the second attachment opening 28. When the bone anchor 10 is connected to the orthopaedic distraction device 24, the first edge row of the row pattern, which includes the first attachment opening 26 and the second attachment opening 28, faces the orthopaedic distraction device 24.

A distance between the first row of the row pattern, which includes the first attachment opening 26 and the second attachment opening 28, and an adjacent second row of the row pattern, which is defined by three fixation openings 14a, 14b, 14c is greater than a distance between the second row of the row pattern and an adjacent third row of the row pattern and greater than a distance between the third row of the row pattern and an adjacent fourth row of the row pattern. In other words, the distance between the first row of the row pattern and the second row of the row pattern is greater than the distances between any further rows of the row pattern.

The distances between the rows in the row pattern following the second row, i.e. the distance between the second row and the third row and the distance between the third row and the fourth row are equal to each other. Similarly, the three rows in the row pattern extending in the second direction perpendicular to the first direction, i.e. a direction perpendicular to the direction of the axis A connecting the first attachment opening 26 and the second attachment opening 28, are equally spaced from each other. The distances between the rows in the row pattern following the second row and extending in the first direction, however, are smaller than the distances between the rows in the row pattern extending in the second direction.

The solid stabilizing portion 36 connecting the first attachment opening 26 and the second attachment opening has a bar-shaped configuration. Similarly, adjacent fixation openings 14 are connected by bar-shaped bridging portions 38. The solid stabilizing portion 36, however, is broader than the bridging portions 38.

The bone anchor 10 further comprises three connecting portions 40a, 40b, 40c extending between the first attachment opening 26 and the adjacent fixation opening 14a, between the solid stabilizing portion 36 and the adjacent fixation opening 14c, and between the second attachment opening 28 and the adjacent fixation opening 14b, respectively. The extension of the connecting portions 40a, 40b, 40c in the direction perpendicular to the axis A connecting the first attachment opening 26 and the second attachment opening 28 depends on the spacing between the first row of openings defined by the first attachment opening 26 and the second attachment opening 28 and the second row of openings defined by the fixation openings 14a, 14b, 14c. Since in the bone anchor 10 according to FIGS. 1 and 2 the spacing between the first row of openings and the second row of openings is greater than the spacing between all rows of openings following the second row of openings, and greater than the spacing between all rows of openings in the row pattern extending in the direction perpendicular to the axis A connecting the first attachment opening 26 and the second attachment opening 28, the connecting portions 40a, 40b, 40c have a greater length than all bridging portions 38.

Figure 3:
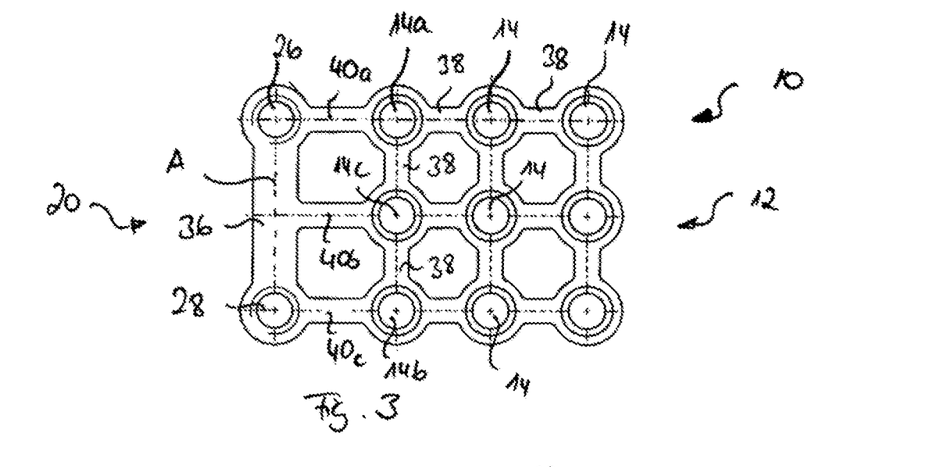
FIG. 3 shows a further embodiment of a bone anchor for use in an orthopaedic procedure.

The bone anchor 10 which is shown in FIG. 3 differs from the anchor according to FIGS. 1 and 2 in that the spacing between the rows of fixation openings 14a, 14b, 14c, 14 extending in the direction of the axis A connecting the first attachment opening 26 and the second attachment opening 28, i.e. the spacing between the rows of openings following the second row of openings is greater and equal to the spacing between the rows of openings extending in the direction perpendicular to the axis A connecting the first attachment opening 26 and the second attachment opening 28. Otherwise, the structure of the bone anchor 10 which is shown in FIG. 3 corresponds to the structure of the anchor according to FIGS. 1 and 2.

Figure 4:
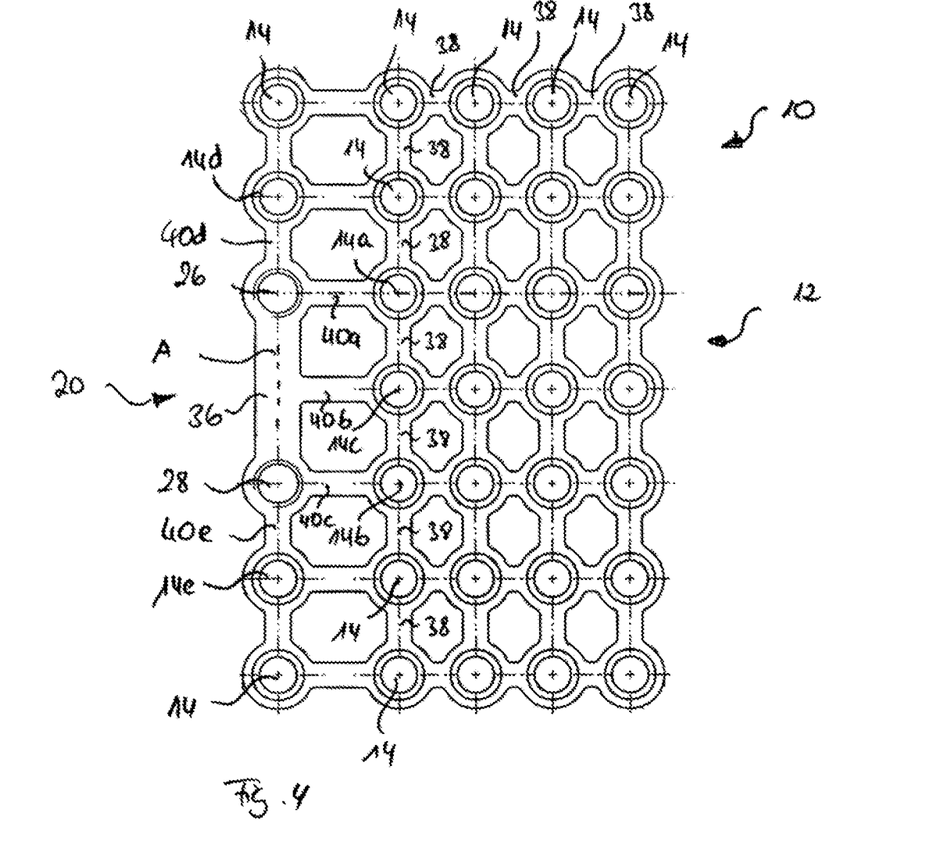
FIG. 4 shows a further embodiment of a bone anchor for use in an orthopaedic procedure.

The bone anchor 10 which is shown in FIG. 4 differs from the anchor according to FIGS. 1 and 2 in that it comprises seven instead of only three rows of openings extending in the direction perpendicular to the axis A connecting the first attachment opening 26 and the second attachment opening 28, and five instead of only four rows of openings extending in the direction of the axis A connecting the first attachment opening 26 and the second attachment opening 28. Further, the first edge row of openings, beside the first attachment opening 26 and the second attachment opening 28 contains four fixation openings 14d, 14e, 14. Hence, an additional connecting portion 40d connects the first attachment opening 26 to an adjacent fixation opening 14d and an additional connecting portion 40e connects the second attachment opening 28 to the adjacent fixation opening 14e. Otherwise, the structure of the bone anchor 10 which is shown in FIG. 4 corresponds to the structure of the anchor according to FIGS. 1 and 2.

Figure 5:
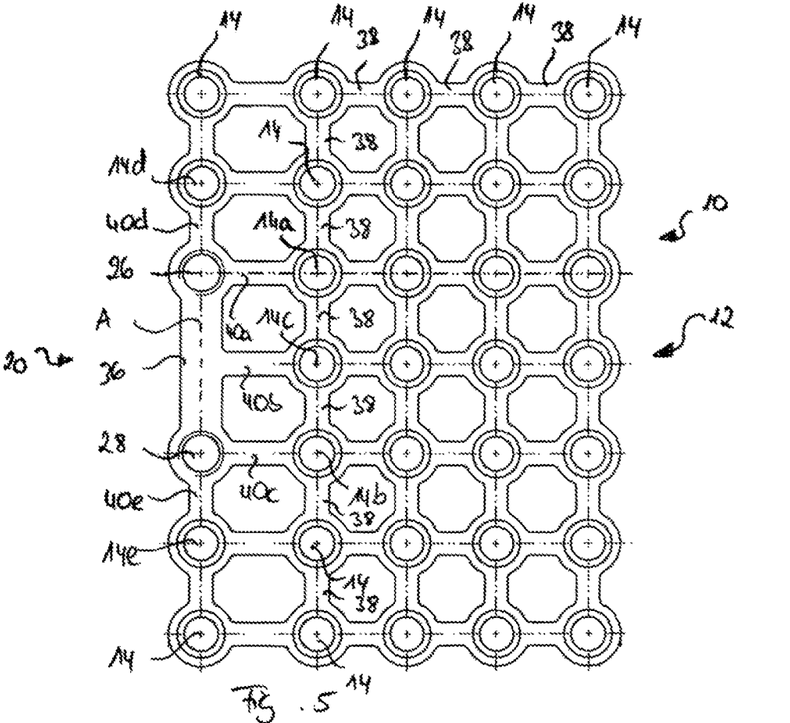
FIG. 5 shows a further embodiment of a bone anchor for use in an orthopaedic procedure.

The bone anchor 10 which is shown in FIG. 5 differs from the anchor according to FIG. 4 in that the spacing between the rows of fixation openings 14a, 14b, 14c, 14 extending in the direction of the axis A connecting the first attachment opening 26 and the second attachment opening 28, i.e. the spacing between the rows of openings following the second row of openings is greater and equal to the spacing between the rows of openings extending in the direction perpendicular to the axis A connecting the first attachment opening 26 and the second attachment opening 28. Otherwise, the structure of the bone anchor 10 which is shown in FIG. 5 corresponds to the structure of the anchor according to FIG. 4.

Figure 6:
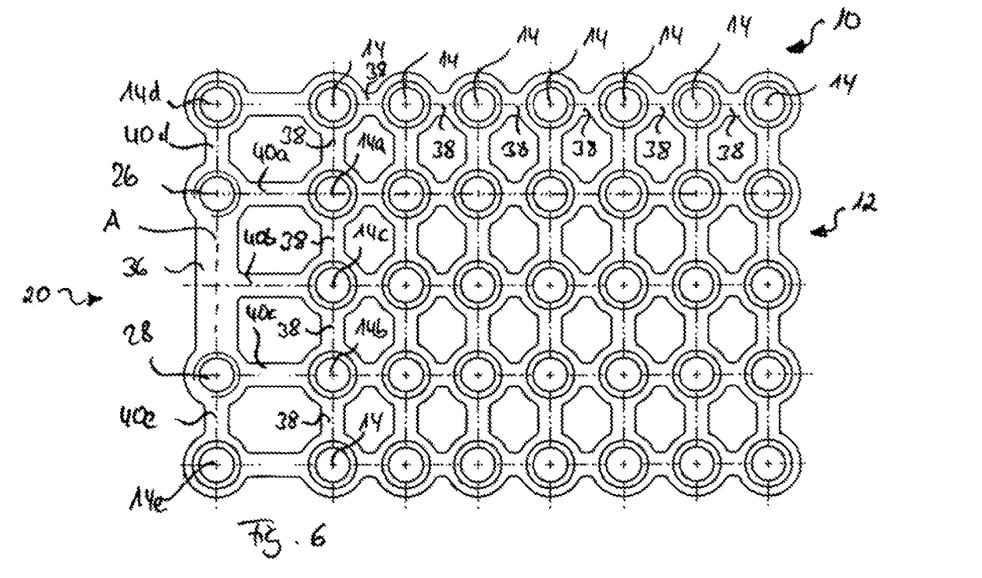
FIG. 6 shows a further embodiment of a bone anchor for use in an orthopaedic procedure.

The bone anchor 10 which is shown in FIG. 6 differs from the anchor according to FIGS. 1 and 2 in that it comprises five instead of only three rows of openings extending in the direction perpendicular to the axis A connecting the first attachment opening 26 and the second attachment opening 28, and eight instead of only four rows of openings extending in the direction of the axis A connecting the first attachment opening 26 and the second attachment opening 28. Further, the first edge row of openings, beside the first attachment opening 26 and the second attachment opening 28, contains two fixation openings 14d, 14e. Hence, an additional connecting portion 40d connects the first attachment opening 26 to the adjacent fixation opening 14d and an additional connecting portion 40e connects the second attachment opening 28 to the adjacent fixation opening 14e. Otherwise, the structure of the bone anchor 10 which is shown in FIG. 6 corresponds to the structure of the anchor according to FIGS. 1 and 2.

Figure 7:
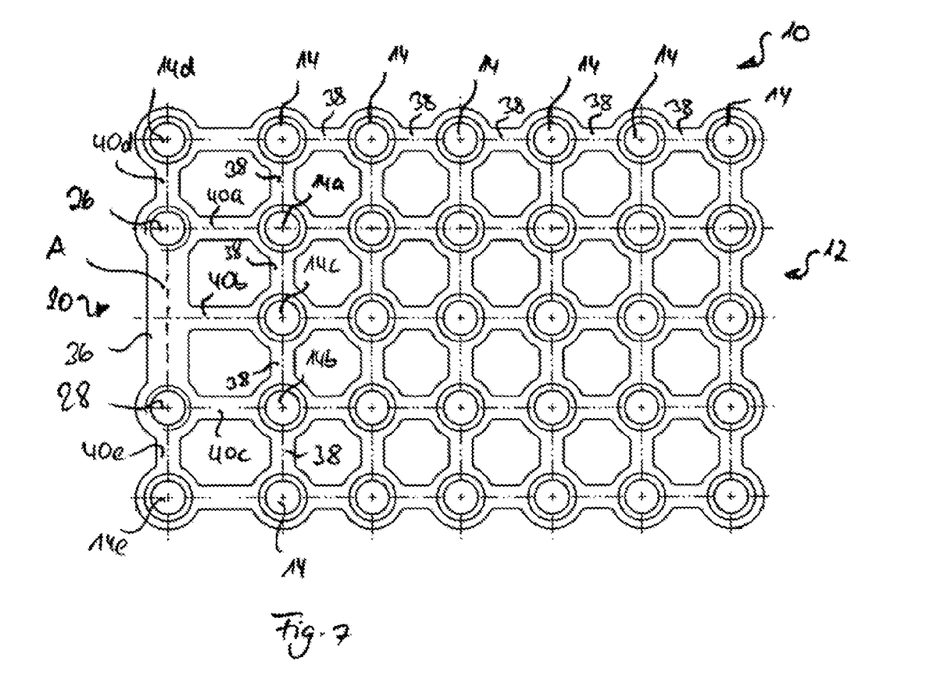
FIG. 7 shows a further embodiment of a bone anchor for use in an orthopaedic procedure.

The bone anchor 10 which is shown in FIG. 7 differs from the anchor according to FIG. 6 in that the spacing between the rows of fixation openings 14a, 14b, 14c, 14 extending in the direction of the axis A connecting the first attachment opening 26 and the second attachment opening 28, i.e. the spacing between the rows of openings following the second row of openings is greater and equal to the spacing between the rows of openings extending in the direction perpendicular to the axis A connecting the first attachment opening 26 and the second attachment opening 28. Otherwise, the structure of the bone anchor 10 which is shown in FIG. 7 corresponds to the structure of the anchor according to FIG. 6.

Figure 8:
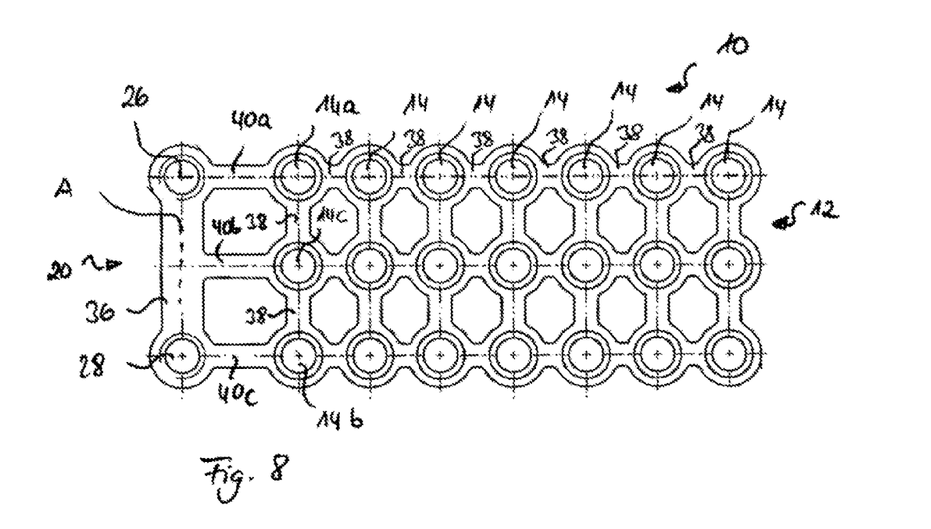
FIG. 8 shows a further embodiment of a bone anchor for use in an orthopaedic procedure.

The bone anchor 10 which is shown in FIG. 8 differs from the anchor according to FIGS. 1 and 2 in that it comprises eight instead of only four rows of openings extending in the direction of the axis A connecting the first attachment opening 26 and the second attachment opening 28. Otherwise, the structure of the bone anchor 10 which is shown in FIG. 6 corresponds to the structure of the anchor according to FIGS. 1 and 2.

Figure 9:
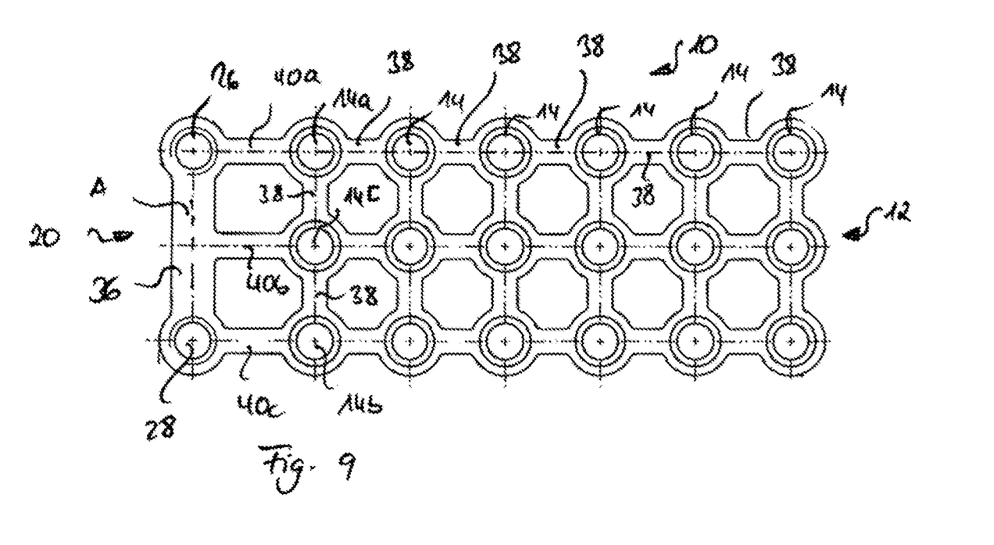
FIG. 9 shows a further embodiment of a bone anchor for use in an orthopaedic procedure.
Figure 10:
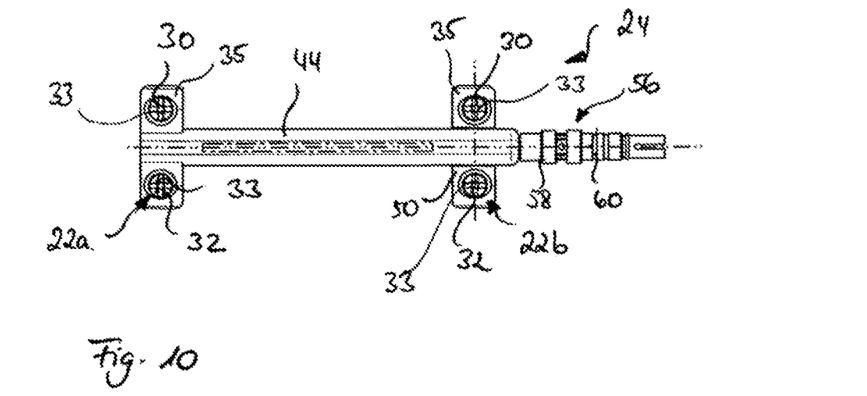
FIG. 10 shows a top view of an embodiment of a distraction device for use in an orthopaedic procedure.

The bone anchor 10 which is shown in FIG. 9 differs from the anchor according to FIG. 8 in that the spacing between the rows of fixation openings 14a, 14b, 14c, 14 extending in the direction of the axis A connecting the first attachment opening 26 and the second attachment opening 28, i.e. the spacing between the rows of openings following the second row of openings is greater and equal to the spacing between the rows of openings extending in the direction perpendicular to the axis A connecting the first attachment opening 26 and the second attachment opening 28. Otherwise, the structure of the bone anchor 10 which is shown in FIG. 9 corresponds to the structure of the anchor according to FIG. 8.

The orthopaedic distraction device 24 according FIGS. 10 to 14 comprises an oblong distractor housing 44 which is open from an underside. The distractor housing 44 consists of titanium. At a distal end the distractor housing 44 is rigidly connected to a fixed bone anchor attachment portion 22a which, like the distractor housing 44, consists of titanium.

A spindle 46, which consists of titanium or steel, extends within the distractor housing 44 and on its outer surface is provided with an external thread. A distal end of the spindle 46 is supported on a respective bearing 48 provided in the fixed bone anchor attachment portion 22a. The bearing 48 is constructed so as to allow a rotation of the spindle 46 relative to the fixed bone anchor attachment portion 22a and the distractor housing 44.

Figure 14:
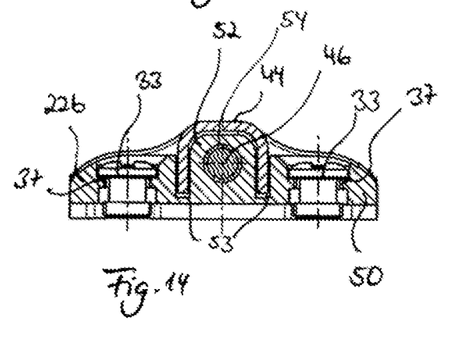
FIG. 14 shows a cross sectional view of the distraction device shown in FIG. 10 in a region of a movable bone anchor attachment portion.

A movable bone anchor attachment portion 22b, also consisting of titanium, comprises a substantially plate-shaped lower portion 50 and a substantially cylindrical upper portion 52 (see in particular FIG. 14). The substantially cylindrical upper portion 52 of the movable bone anchor attachment portion 22b is disposed inside the distractor housing 44, whereas the substantially plate-shaped lower portion 50 of the movable bone anchor attachment portion 22b laterally extends from the distractor housing 44. A through hole 54 extends through the cylindrical upper portion 52 and on its inner surface is provided with an internal thread. The spindle 46 extends through the through hole 54 formed in the cylindrical upper portion 52 of the movable bone anchor attachment portion 22b such that the external thread provided on the outer surface of the spindle 46 engages with the internal thread provided on the inner surface of the through hole 54.

Upon rotation of the spindle 46 the movable bone anchor attachment portion 22b is displaced in a longitudinal direction relative to the spindle 46, the distractor housing 44 and the fixed bone anchor attachment portion 22b. The displacement of the movable bone anchor attachment portion 22b is guided by lower edges of the distractor housing 44 interacting with a groove 53 formed in the substantially plate-shaped lower portion 50 of the movable bone anchor attachment portion 22b. A rotation or a pivotal movement of the movable bone anchor attachment portion 22b relative to the housing 44 and/or the fixed bone anchor attachment portion 22a thus is prevented. Further, the design of the movable bone anchor attachment portion 22b in connection with the design of the housing 44 allows to achieve a particularly flat geometry of the orthopaedic distraction device 24.

The orthopaedic distraction device 24 has a push/pull-functionality which means that the movable bone anchor attachment portion 22b, dependent on the sense of rotation of the spindle 46, can be displaced longitudinally relative to the spindle 46, the distractor housing 44 and the fixed bone anchor attachment portion 22a in a distal direction or a proximal direction. In other words, dependent on the sense of rotation of the spindle 46, the distance between the movable bone anchor attachment portion 22b and the fixed bone anchor attachment portion 22a can be increased or decreased as desired.

The attachment devices 33 are received in the attachment openings 30, 32 of the fixed bone anchor attachment portion 22a and the movable bone anchor attachment portion 22b in a loss-proof manner. As becomes apparent from FIG. 14, the loss-proof fixation of the attachment devices 33 in the attachment openings 30, 32 is achieved by providing the internal thread 37 with a portion having a reduced cross-section.

Figure 11:
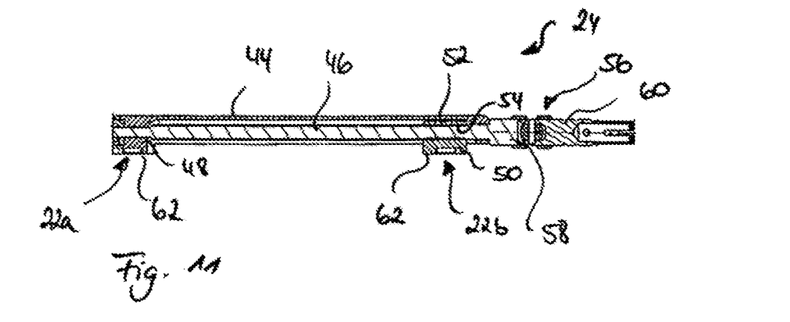
FIG. 11 shows a sectional view of the distraction device shown in FIG. 10 along a longitudinal axis of the distraction device.

A proximal end of the spindle 46, which extends from the through hole 54 formed in the cylindrical upper portion 52 of the movable bone anchor attachment portion 22b, is rigidly connected to a cardan joint 56. The cardan joint 56 has a first section 58 attached to the spindle 46 and a second section 60 pivotally connected to the first section 58 such that the second section 60 can be pivoted relative to the first section 58 about an angle of 45°. At its free end the second section 60 of the cardan joint 60 is provided with a coupling device which allows the coupling of a first end of a removable activation rod (not shown) to the cardan joint 60 and hence the spindle 46. The activation rod may be a fixed rod or a flexible rod. In any case, a second end of the activation rod can be connected to a socket wrench. By means of the socket wrench a user can apply a torque to the activation rod which, via the cardan joint 60, is transferred to the spindle 46 and hence induces a rotation of the spindle 46.

Figure 12:
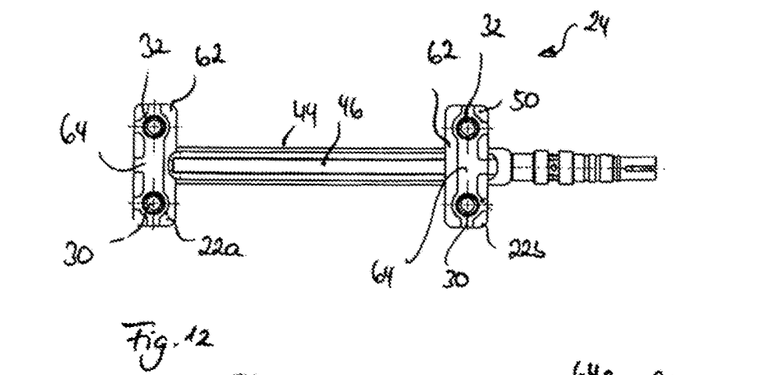
FIG. 12 shows a bottom view of the distraction device according to FIG. 10.
Figure 13:
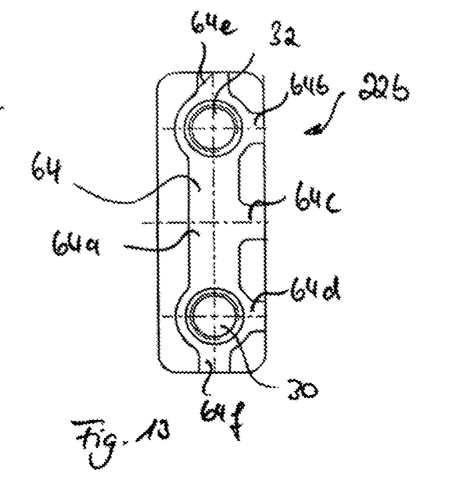
FIG. 13 shows a detail bottom view of a bone anchor attachment portion of the distraction device according to FIG. 10.

A contact surface 62 of the bone anchor attachment portions 22a, 22b of the orthopaedic distraction device 24 with the bone anchor 10, i.e. the device attachment portion 20 of the bone anchor 10, is provided with a recess 64, the shape of which is adapted to the shape of the device attachment portion 20 of the bone anchor 10 (see FIGS. 12 and 13). In particular, the recess 64 has a portion 64a adapted to receive the solid stabilizing portion 36 connecting the first attachment opening 28 and the second attachment opening 28 provided in the device attachment portion 20 of the bone anchor 10. Further, the recess 64 has portions 64b to 64f adapted to receive parts of the connecting portions 40a to 40e extending between the first attachment opening 26 and the adjacent fixation openings 14a, 14d between the solid stabilizing portion 36 and the adjacent fixation opening 14c and between the second attachment opening 28 and the adjacent fixation openings 14b, 14e of the bone anchor 10.

The depth of the recess 64 provided in the contact surface 62 of the bone anchor attachment portions 22a, 22b with the bone anchor 10 is selected such that the device attachment portion 20 of the bone anchor 10 is entirely received in the recess. In other words, the depth of the recess 64 provided in the contact surface 62 of the bone anchor attachment portions 22a, 22b with the bone anchor 10 is selected such that a surface of the device attachment portion of the bone anchor 10 is disposed flush with portions of the contact surface 62 surrounding the recess 64, when the bone anchor 10 is attached to a bone anchor attachment portion 22a, 22b.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopaedic system for use in an orthopaedic procedure comprising:
   an orthopaedic device having a bone anchor attachment portion with a first attachment opening and a second attachment opening; and
   a bone anchor having:
      a bone fixation portion provided with a plurality of fixation openings, the fixation openings each being adapted to receive a fixation device for fixing the bone fixation portion to a bone of a patient; and
      a device attachment portion provided with a first attachment opening and a second attachment opening, each of the first attachment opening and the second attachment opening of the device attachment portion being connected to each other and spanned by a solid stabilizing portion without openings,
   wherein the first attachment opening and the second attachment openings of the device attachment portion are disposed in a first row of a row pattern,
   wherein the plurality of fixation openings are disposed in at least a second row of the row pattern disposed adjacent and parallel to the first row of the row pattern,
   wherein adjacent fixation openings of the bone fixation portion are connected by a bar-shaped bridging portion,
   wherein the solid stabilizing portion has a bar-shaped configuration and is broader and longer than the bar-shaped bridging portion,
   wherein each of the first and second attachment openings of the device attachment portion are adapted to receive an attachment device for attaching the device attachment portion to the bone anchor attachment portion,
   wherein a contact surface of the bone anchor attachment portion of the orthopaedic device is provided with a recess having a shape adapted to receive a corresponding shape of the device attachment portion of the bone anchor, and
   wherein a depth of the recess is selected such that the device attachment portion of the bone anchor is entirely received in the recess.

2. The orthopaedic system according to claim 1, wherein a distance between the first attachment opening and the second attachment opening of the device attachment portion is greater than a distance between the first attachment opening of the device attachment portion and an adjacent fixation opening of the bone fixation portion.

3. The orthopaedic system according to claim 1, wherein a distance between the first attachment opening and the second attachment opening of the device attachment portion is greater than a distance between the second attachment opening of the device attachment portion and an adjacent fixation opening of the bone fixation portion.

4. The orthopaedic system according to claim 1, wherein a distance between the first row of the row pattern and a second row of the at least a second row of the row pattern is greater than a distance between the second row of the row pattern and an adjacent third row of the at least a second row of the row pattern.

5. The orthopaedic system according to claim 1, wherein the first row of the row pattern forms an edge row of the row pattern.

6. The orthopaedic system according to claim 1, further comprising at least one connecting portion extending between the first attachment opening of the device attachment portion and an adjacent fixation opening of the bone fixation portion.

7. The orthopaedic system according to claim 1, further comprising at least one connecting portion extending between the solid stabilizing portion of the device attachment portion and an adjacent fixation opening of the bone fixation portion.

8. The orthopaedic system according to claim 1, further comprising at least one connecting portion extending between the second attachment opening of the device attachment portion and an adjacent fixation opening of the bone fixation portion.

9. The orthopaedic system according to claim 1, wherein at least one of the first attachment opening and the second attachment opening of the device attachment portion is provided with an internal thread.

10. An orthopaedic system for use in an orthopaedic procedure comprising:
   an orthopaedic device having:
      a treatment portion adapted to perform a desired orthopaedic treatment to a bone of a patient;
      a first bone anchor attachment portion; and
      a second bone anchor attachment portion that is moveable relative to the first bone attachment portion; and
   a bone anchor including:
      a bone fixation portion provided with a plurality of fixation openings, the fixation openings each being adapted to receive a fixation device for fixing the bone fixation portion to a bone of a patient; and
      a device attachment portion provided with a first attachment opening and a second attachment opening, each of the first attachment opening and the second attachment openings of the device attachment portion being connected to each other by a solid stabilizing portion without openings,
   wherein the first attachment opening and the second attachment opening of the device attachment portion are disposed in a first row of a row pattern,
   wherein the plurality of fixation openings of the bone fixation portion are disposed in at least a second row of the row pattern disposed adjacent and parallel to the first row of the row pattern, wherein a distance between the first row of the row pattern and a second row of the at least a second row of the row pattern is greater than a distance between the second row of the row pattern and an adjacent third row of the row pattern, wherein each of the first attachment opening and the second attachment opening of the device attachment portion are adapted to receive an attachment device for attaching the device attachment portion to the first bone anchor attachment portion, wherein a contact surface of the first bone anchor attachment portion of the orthopaedic device is provided with a recess having a shape adapted to receive a corresponding shape of the device attachment portion of the bone anchor, and wherein a depth of the recess is selected such that the device attachment portion of the bone anchor is entirely received in the recess.

11. The orthopaedic system of claim 10, wherein the attachment device is a clip.

12. An orthopaedic system for use in an orthopaedic procedure comprising:
an orthopaedic device having:
a treatment portion adapted to perform a desired orthopaedic treatment to a bone of a patient,
a first bone anchor attachment portion with a first attachment opening and a second attachment opening, and
a second bone anchor attachment portion,
wherein the first bone anchor attachment portion is moveable relative to the second bone anchor attachment portion; and
a bone anchor having:
a bone fixation portion provided with a plurality of fixation openings, the fixation openings each being adapted to receive a fixation device for fixing the bone fixation portion to a bone of a patient; and
a device attachment portion provided with a first attachment opening and a second attachment opening, the first attachment opening and the second attachment opening being connected to each other and spanned by a solid stabilizing portion without openings,
wherein the first attachment opening and the second attachment opening of the device attachment portion are disposed in a first row of a row pattern,
wherein the plurality of fixation openings of the bone fixation portion are disposed in at least a second row of the row pattern disposed adjacent and parallel to the first row of the row pattern,
wherein a distance between the first row of the row pattern and a second row of the at least a second row of the row pattern is greater than a distance between the second row of the row pattern and an adjacent third row of the row pattern,
wherein each of the first and second attachment openings of the device attachment portion are adapted to receive an attachment device for fixing the device attachment portion to the first bone anchor attachment portion,
wherein a contact surface of the first bone anchor attachment portion of the orthopaedic device is provided with a recess having a shape adapted to receive a corresponding shape of the device attachment portion of the bone anchor, and
wherein a depth of the recess is selected such that the device attachment portion of the bone anchor is entirely received in the recess.

13. The orthopaedic system according to claim 12, wherein a distance between the first attachment opening and the second attachment opening of the device attachment portion is greater than a distance between the first attachment opening of the device attachment portion and an adjacent fixation opening of the bone fixation portion.

14. The orthopaedic system according to claim 12, wherein a distance between the first attachment opening and the second attachment opening of the device attachment portion is greater than a distance between the second attachment opening of the device attachment portion and an adjacent fixation opening of the bone fixation portion.

15. The orthopaedic system according to claim 12, wherein the first row of the row pattern forms an edge row of the row pattern.

16. The orthopaedic system according to claim 12, further comprising at least one connecting portion extending between the first attachment opening of the device attachment portion and an adjacent fixation opening of the bone fixation portion.

17. The orthopaedic system according to claim 12, further comprising at least one connecting portion extending between the solid stabilizing portion of the device attachment portion and an adjacent fixation opening of the bone fixation portion.

18. The orthopaedic system according to claim 12, further comprising at least one connecting portion extending between the second attachment opening of the device attachment portion and an adjacent fixation opening of the bone fixation portion.

19. The orthopaedic system according to claim 12, wherein at least one of the first attachment opening and the second attachment opening of the device attachment portion is provided with an internal thread.

* * * * *